(12) United States Patent
Tsuji et al.

(10) Patent No.: US 6,506,914 B1
(45) Date of Patent: Jan. 14, 2003

(54) PROCESS FOR PRODUCING OXIRANE COMPOUND

(75) Inventors: Junpei Tsuji, Ichihara (JP); Carsten Stocker, Meerbusch (DE)

(73) Assignee: Sumitomo Chemical Company, Limited, Osaka (JP)

( * ) Notice: Subject to any disclaimer, the term of this patent is extended or adjusted under 35 U.S.C. 154(b) by 337 days.

(21) Appl. No.: 10/069,238

(22) PCT Filed: Aug. 21, 2000

(86) PCT No.: PCT/JP00/05603

§ 371 (c)(1),
(2), (4) Date: May 31, 2002

(87) PCT Pub. No.: WO01/14356

PCT Pub. Date: Mar. 1, 2001

(30) Foreign Application Priority Data

Aug. 25, 1999 (JP) ............................................. 11-238541

(51) Int. Cl.⁷ ....................... C07D 301/19; C07B 61/00; B01J 21/08
(52) U.S. Cl. ........................................ 549/529; 549/531
(58) Field of Search .......................................... 549/529

(56) References Cited

U.S. PATENT DOCUMENTS

| | | | | |
|---|---|---|---|---|
| 3,829,392 A | * | 8/1974 | Wulff | .......................... 252/430 |
| 3,923,843 A | * | 12/1975 | Wulff | |
| 4,176,089 A | * | 11/1979 | Neville | ........................ 252/452 |
| 4,367,342 A | | 1/1983 | Wulff et al. | |
| 5,081,267 A | | 1/1992 | Rameswaran et al. | |
| 5,935,895 A | | 8/1999 | Baiker et al. | |

FOREIGN PATENT DOCUMENTS

| | | | |
|---|---|---|---|
| JP | 0 659 685 A1 | | 6/1995 |
| WO | 9609117 | * | 3/1996 |

OTHER PUBLICATIONS

H. Kochkar et al., "Synthesis of Hydrophobic $TiO_2$–$SiO_2$ Mixed Oxides for the Epoxidation of Cyclohexene", *Journal of Catalysis,* vol. 171, 1997, pp. 420–430.

C. A. Müller et al., "Organically Modified Titania–Silica Aerogels for the Epoxidation of Olefins and Allylic Alcohols", *Journal of Catalysis,* vol. 184, 1999, pp. 280–293.

* cited by examiner

Primary Examiner—Sabiha Qazi
(74) Attorney, Agent, or Firm—Sughrue Mion, PLLC

(57) ABSTRACT

A process for producing an oxirane compound by reacting an olefin with hydroperoxides in the presence of a catalyst wherein said catalyst is obtained by gelling a silicon compound of the following formula (1) (silicon compound (1)), a silicon compound of the following formula (2) (silicon compound (2)) and a titanium compound in water, alcohol solvent or mixed solvent of water and alcohol, removing a solvent in the resulted gel by extraction with supercritical fluid, then, performing drying and silylation treatment:

$$Si(OR^1)_4 \qquad (1)$$

$$(R^2)_m Si(OR^3)_{4-m} \qquad (2)$$

($R^1$, $R^2$ and $R^3$ independently represent a hydrocarbon group having 1 to 20 carbon atoms. m represents an integer of 1 or 2.)

5 Claims, No Drawings

PROCESS FOR PRODUCING OXIRANE COMPOUND

This application ia a 371 of PCT/JP00/05603 filed on Aug. 21, 2000.

TECHNICAL FIELD

The present invention relates to a process for producing an oxirane compound. More particularly, the present invention relates to a process for producing an oxirane compound in which the oxirane compound can be obtained with high selectivity and high yield by reacting an olefin with a hydroperoxide in the presence of a catalyst.

BACKGROUND ART

A process for obtaining an oxirane compound by reacting an olefin with a hydroperoxide in the presence of a catalyst is known. For example, in U.S. Pat. No. 4367342, a method of using a titanium-supported silica catalyst is described. In the conventional method, however, the selectivity and yield of oxirane compound as the intended material, were insufficient.

DISCLOSURE OF THE INVENTION

Under such conditions, the present inventors have intensively studied regarding a process for producing an oxirane compound having no problem as described above, and resultantly found that an oxirane compound can be obtained under high selectivity and high yield by reacting an olefin with a hydroperoxide using a catalyst obtained by a specific method, leading to completion of the invention.

Namely, the present invention relates to a process for producing an oxirane compound by reacting an olefin with a hydroperoxide in the presence of a catalyst, wherein the catalyst is obtained by gelling a silicon compound of the following formula (1) (silicon compound (1)), a silicon compound of the following formula (2) (silicon compound (2)) and a titanium compound in water, alcohol solvent or mixed solvent of water and alcohol, removing the solvent in the resulted gel by extraction with supercritical fluid, then, drying and silylating the resultant:

  (1)

  (2)

($R^1$, $R^2$ and $R^3$ independently represent a hydrocarbon group having 1 to 20 carbon atoms and m represents an integer of 1 or 2.).

BEST MODE FOR CARRYING OUT THE INVENTION

As the olefin to be subjected to reaction, ethylene, propylene, 1-butene, 2-butene, isobutylene, butadiene, 1-pentene, isoprene, 1-hexene, 1-octane, 1-decene, cyclopentene, cyclohexene, styrene, allyl chloride, allyl alcohol and the like are exemplified.

As the hydroperoxide to be subjected to reaction, any of organic hydroperoxides and inorganic hydroperoxides can be used. As the organic hydroperoxide, ethylbenzene hydroperoxide, cumene hydroperoxide, t-butylhydroperoxide and the like are exemplified. As the inorganic hydroperoxide, hydrogen peroxide and the like are exemplified.

From the industrial standpoint, a process for producing propylene oxide from propylene and an organic hydroperoxide is important, and the catalyst according to the present invention can be suitably used in this reaction.

In the present invention, there is used a catalyst obtained by gelling a silicon compound of the following formula (1) (silicon compound (1)), a silicon compound of the following formula (2) (silicon compound (2)) and a titanium compound in water, an alcohol solvent or a mixed solvent of water and an alcohol, removing the solvent in the resulted gel by extraction with supercritical fluid, then, drying and silylating the resultant:

  (1)

  (2)

wherein $R^1$, $R^2$ and $R^3$ independently represent a hydrocarbon group having 1 to 20 carbon atoms. m represents an integer of 1 or 2. As the hydrocarbon group, a methyl group, ethyl group, propyl group, butyl group, phenyl group, benzyl group and the like are exemplified, and these hydrocarbon groups may be partially substituted with a hetero atom. Preferable are a methyl group, ethyl group, propyl group, butyl group and phenyl group which are easily available in industrial.

Specific preferable examples of the silicon compound (1) include tetramethyl orthosilicate, tetraethyl orthosilicate, tetrapropyl orthosilicate, tetraisopropyl orthosilicate, tetrabutyl orthosilicate and the like. Specific preferable examples of the silicon compound (2) include trimethoxymethylsilane, trimethoxyphenylsilane, dimethoxydimethylsilane, triethoxymethylsilane, triethoxyphenylsilane and the like.

The ratio of the mol number of the hydrocarbon group $R^2$ to the total mol number of the silicon compound (1) and silicon compound (2) is preferably from 5 to 95%, further preferably from 20 to 80%. When the ratio is too small, catalytic ability may decrease, on the other hand, when too large, gelling may not progress in catalysis synthesis.

As the titanium compound, titanium alkoxides, for example, tetramethyl orthotitanate, tetraethyl orthotitanate, tetrapropyl orthotitanate, tetraisopropyl orthotitanate, tetrabutyl orthotitanate, titanium diisopropoxide bis (acetylacetonate) and the like can be Exemplified.

Examples of alcohols as the solvent include methanol, ethanol, n-propanol, isopropanol, butanol, cyclohexanol, ethylene glycol and the like.

The catalyst in the present invention is prepared as described below. First, a silicon compound (1), a silicon compound (2) and a titanium compound are gelled in water, an alcohol solvent, or a mixed solvent of water and an alcohol. It is preferable to adjust so that the ratio of the mol number of the hydrocarbon group $R^2$ to the total mol number of the silicon. compound (1) and silicon compound (2) becomes 5 to 95%. The silicon compound (1) and silicon compound (2) may each be a mixture of two or more compounds. The molar ratio of a titanium compound used to the total mol number of the silicon compound (1) and silicon compound (2) is preferably from 0.0001 to 1. As the gelling method, the following methods are illustrated. That is, usually by adding an acid or alkali as a promoter into water, the alcohol solvent or the mixed solvent of water and alcohol containing a silicon compound (1), silicon compound (2) and titanium compound dissolved, hydrolysis and condensing reaction of the silicon compounds and titanium compound can be progressed, and finally, a gel which is a polymer condensate containing a Si—O—Ti bond can be obtained. The gelling reaction is usually conducted at temperatures from −30 to 100° C. Aging may also be effected to grow gelled solid. The aging is usually conducted at 0 to 200° C. within 180 hours. An acid or alkali is used as a promoter of the above-mentioned hydrolysis and condensing reaction, and use of an acid is preferable from the standpoint of the resulting catalytic ability. Examples of the acid include inorganic acids such as nitric acid, hydrochloric acid, sulfuric acid and the like and organic acids such as formic acid, acetic acid and the like, and examples of the alkali include sodium hydroxide, potassium hydroxide, ammonia and the like. The addition amount of this acid or alkali cannot be limited since it depends on the kinds of raw material compounds and gelling conditions, and it is preferable that the addition amount is generally in the range from 0.0001 to 100 mol based on 1 mol of silicon compounds.

The solvent in the resulted gel is removed by extraction with supercritical fluid. As the fluid, carbon dioxide, methanol, ethanol, propanol and the like are exemplified, and use of carbon dioxide is preferable since post treatment is easy and high catalytic ability is obtained. As the method of removal by extraction, the following methods are listed. Namely, the removal by extraction can be carried out by passing supercritical carbon dioxide through an autoclave charged with the gel under conditions for forming supercritical carbon dioxide, namely, at temperatures of about 31° C. or more and under pressure of about 7.3 MPa or more. For example, supercritical carbon dioxide fluid having a temperature of 31 to 100° C. and a pressure of 10 to 30 MPa can be used. By this operation, water, the alcohol solvent or mixed solvent of water and the alcohol incorporated into the gel can be removed by extraction.

After the above-mentioned extraction removal operation, drying and silylation are performed.

The drying is preferably conducted under reduced pressure or under gas flow of air, nitrogen or the like at 0 to 200° C.

The silylation is preferably conducted by contacting a dried catalyst obtained in the former step with a silylating agent in a solvent or gas phase at temperatures from 20 to 300° C., to convert a hydroxyl group existing on the surface of the catalyst into a silyl group. By performing this silylation treatment, the catalytic ability can be improved. Examples of the silylating agent include organic silanes such as chlorotrimethylsilane, dichlorodimethylsilane, chlorotriethylsilane and the like, organic silylamines such as N-trimethylsilylimidazole, N-t-butyldimethylsilylimidazole, N-trimethylsilyldimethylamine and the like, organic silylamides such as N,O-bistrimethylsilylacetoamide, N-trimethylsilylacetoamide and the like, organic silazanes such as hexamethyldisilazane, heptamethyldisilazane and the like. Hexamethyldisilazane is a preferable silylating agent.

Thus, the catalyst according to the present invention can be obtained.

The process of the present invention is a process for producing an oxirane compound in which an olefin with a hydroperoxide are reacted in the presence of the above-mentioned catalyst. This epoxidation reaction can be conducted by contacting an olefin and hydroperoxides with a catalyst. This reaction can be carried out in liquid phase in the presence or absence of a suitable solvent. As the solvent, compounds inert to the reaction and excellent in solubility of an olefin and/or a hydroperoxide can be used. As specific examples of the solvent in the case of use of an organic hydroperoxide, hydrocarbons such as butane, octane, benzene, toluene, ethylbenzene, cumene and the like are listed. On the other hand, as specific examples of the solvent in the case of use of an inorganic hydroperoxide, methanol, ethanol, isopropanol, t-butanol, water and the like are listed.

The epoxidation reaction can be conducted usually at temperatures of from 0 to 200° C. The pressure may advantageously be a pressure for maintaining a reaction mixture at liquid condition, and generally from 0.1 to 10 MPa. The epoxidation reaction can be carried out by using a powder catalyst or molded catalyst in a slurry or fixed bed according to a batch-wise method, semi-continuous method or continuous method.

EXAMPLES

The present invention is illustrated by the following examples.

Example 1

Into a 300 ml flask were charged 18.26 g of tetramethyl orthosilicate, 7.00 g of trimethoxymethylsilane 2.31 g of tetra-n-butyl orthotitanate and 65 ml of n-propanol. To this solution was added a mixed solution of 30 ml of 70% nitric acid and 35 ml of n-propanol from a dropping funnel while stirring the solution at 25° C. over about 1 hour. This solution was left over night and day at 25° C. to obtain a gel. The resulted gel was transferred to an autoclave, and a solvent in the gel was removed by extraction by passing supercritical carbon dioxide of 45° C. and 24 MPa at a rate of 8 g/min. for about 12 hours. Subsequently, the gel was dried under reduced pressure of about 100 Pa at 25° C. for 10 hours. This dried solid was filled in a flow apparatus made of glass, heated at 200° C., and a mixed gas prepared by diluting a vapor of hexamethyldisilazane with an excess nitrogen gas was passed for 3 hours, to conduct silylation treatment, obtaining about 12 g of a catalyst.

The epoxidation reaction test was conducted according to the following conditions. In an autoclave was charged 1 g of the catalyst, 17 g of propylene, and 24 g of a 35% solution of ethylbenzene hydroperoxide in ethylbenzene, and they were reacted at 80° C. for 1.5 hours with stirring. The reaction solution was analyzed, and the reaction performance was checked. The results are shown in Table 1.

Examples 2 to 4

The same procedure as in Example 1 was conducted excepting the charging ratio of trimethoxymethylsilane in silicon compounds was changed. The results are shown in Table 1.

Comparative Example 1

The same procedure as in Example 1 was conducted excepting trimethoxymethylsilane was not added. The results are shown in Table 2.

Comparative Example 2

The silylation treatment was not conducted in Example 1. The results are shown in Table 2.

Comparative Example 3

The silylation treatment was not conducted in Example 2. The results are shown in Table 2.

TABLE 1

| | Example | | | |
|---|---|---|---|---|
| | 1 | 2 | 3 | 4 |
| Ratio (%) of MeSi(OMe)$_3$ | 30 | 40 | 50 | 10 |
| Presence or absence of silylation treatment | Presence | Presence | Presence | Presence |
| Reaction performance | | | | |
| EBHP conversion (%) | 98.7 | 98.4 | 96.1 | 97.3 |
| PO selectivity (%) | 94.0 | 94.5 | 96.4 | 94.1 |

TABLE 2

| | Comparative Example | | |
|---|---|---|---|
| | 1 | 2 | 3 |
| Ratio (%) of MeSi(OMe)$_3$ | 0 | 30 | 40 |
| Presence or absence of silylation treatment | Presence | Absence | Absence |
| Reaction performance | | | |
| EBHP conversion (%) | 91.8 | 94.6 | 96.5 |
| PO selectivity (%) | 95.0 | 88.1 | 89.0 |

Explanation of Tables

Ratio (%) of MeSi(OMe)$_3$: ratio of mol number of MeSi(OMe)$_3$ to total mol number of Si(OMe)$_4$ and MeSi(OMe)$_3$ charged EBHP conversion: [reacted EBHP (ethylbenzene hydroperoxide)/fed EBHP]×100 (%)

PO selectivity: [produced PO (propylene oxide)(mol)/reacted EBHP (mol)]×100 (%)

Example 5

Into a 300 ml flask were charged 18.27 g of tetramethyl orthosilicate, 6.18 g of dimethoxydimethylsilane, 2.31 g of tetra-n-butyl orthotitanate and 65 ml of n-propanol. The ratio of the mol number of a Me—Si group (corresponding to hydrocarbon group R$^2$ in silicon compound (2)) in dimethoxydimethylsilane to the total mol number of silicon compounds in this experiment was 60%. To this solution were added a mixed solution of 26 ml of 70% nitric acid and 35 ml of n-propanol from a dropping funnel while stirring the solution at 25° C. over about 1 hour. This solution was left over night and day at 25° C. to obtain a gel. The resulted gel was transferred to an autoclave, and a solvent in the gel was removed by extraction by passing supercritical carbon dioxide of 45° C. and 24 MPa at a rate of 5 g/min. for about 12 hours. Subsequently, the gel was dried under reduced pressure of about 100 Pa at 25° C. for 10 hours. This dried solid was filled in a flow apparatus made of glass, heated at 200° C., and a mixed gas prepared by diluting a vapor of hexamethyldisilazane with an excess nitrogen gas was passed for 3 hours, to conduct silylation treatment, obtaining about 12 g of a catalyst.

The epoxidation reaction test was conducted according to the following conditions. In an autoclave were charged 1 g of the catalyst, 17 g of propylene, and 24 g of a 35% solution of ethylbenzene hydroperoxide in ethylbenzene, and they were reacted at 80° C. for 1.5 hours under stirring, to obtain performance of an EBHP conversion of 98.4% and a PO selectivity of 95.5%.

Comparative Example 4

The silylation treatment was not conducted in Example 5. The reaction performance showed an EBHP conversion of 98.2% and a PO selectivity of 90.7%.

Industrial Applicability

As described above, according to the present invention, it becomes possible to provide a process for producing an oxirane compound in which an olefin and hydroperoxides can be reacted in the presence of a catalyst to obtain an oxirane compound under high selectivity and yield.

What is claimed is:

1. A process for producing an oxirane compound by reacting an olefin and a hydroperoxide in the presence of a catalyst wherein said catalyst is obtained by gelling a silicon compound of the following formula (1) (silicon compound (1)), a silicon compound of the following formula (2) (silicon compound (2)) and a titanium compound in water, alcohol solvent or mixed solvent of water and alcohol, removing a solvent in the resulted gel by extraction with supercritical fluid, then, drying and silylating the resultant:

$$Si(OR^1)_4 \qquad (1)$$

$$(R^2)_m Si(OR^3)_{4-m} \qquad (2)$$

(R$^1$, R$^2$ and R$^3$ independently represent a hydrocarbon group having 1 to 20 carbon atoms and m represents an integer of 1 or 2).

2. The process according to claim 1, wherein the ratio of the mol number of the hydrocarbon group R$^2$ to the total mol number of the silicon compound (1) and silicon compound (2) is from 5 to 95%.

3. The process according to claim 1, wherein the supercritical fluid is supercritical fluid of carbon dioxide.

4. The process according to claim 1, wherein the olefin is propylene.

5. The process according to claim 1, wherein the hydroperoxide is an organic hydroperoxide.

* * * * *

UNITED STATES PATENT AND TRADEMARK OFFICE
CERTIFICATE OF CORRECTION

PATENT NO.   : 6,506,914 B1
DATED        : January 14, 2003
INVENTOR(S)  : Tsuji et al.

It is certified that error appears in the above-identified patent and that said Letters Patent is hereby corrected as shown below:

<u>Title page,</u>
Item [*] Notice, "Subject to any disclaimer, the term of this patent is extended or adjusted under 35 USC 154(b) by (337) days", delete the phrase "by 337 days" and insert -- by 0 days --

Signed and Sealed this

Fourteenth Day of October, 2003

JAMES E. ROGAN
*Director of the United States Patent and Trademark Office*